(12) United States Patent
DiFoggio (10) Patent No.: US 9,720,122 B2
(45) Date of Patent: Aug. 1, 2017

(54) REFLECTION-ONLY SENSOR AT MULTIPLE ANGLES FOR NEAR REAL-TIME DETERMINATION OF ACOUSTIC PROPERTIES OF A FLUID DOWNHOLE

(71) Applicant: Baker Hughes Incorporated, Houston, TX (US)

(72) Inventor: Rocco DiFoggio, Houston, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 380 days.

(21) Appl. No.: 14/339,240

(22) Filed: Jul. 23, 2014

(65) Prior Publication Data

US 2016/0025884 A1    Jan. 28, 2016

(51) Int. Cl.
| | |
|---|---|
| *G01V 1/50* | (2006.01) |
| *E21B 47/00* | (2012.01) |
| *G01H 5/00* | (2006.01) |
| *G01V 1/40* | (2006.01) |
| *E21B 47/01* | (2012.01) |

(52) U.S. Cl.
CPC ............ *G01V 1/50* (2013.01); *E21B 47/0005* (2013.01); *E21B 47/011* (2013.01); *G01H 5/00* (2013.01); *G01V 1/40* (2013.01)

(58) Field of Classification Search
CPC ... G01V 1/50; G01V 1/48; G01V 1/40; G01H 5/00; E21B 47/0005; E21B 47/011;
(Continued)

(56) References Cited

U.S. PATENT DOCUMENTS

| | | | | |
|---|---|---|---|---|
| 3,103,640 A | * | 9/1963 | Lockhart | H03H 9/38 333/144 |
| 3,311,854 A | * | 3/1967 | Mason | H03H 9/19 310/334 |

(Continued)

OTHER PUBLICATIONS

Int'l Search Report and Written Opinion in PCT/US2015/041072 dtd Mar. 28, 2016.

*Primary Examiner* — Robert Huber
*Assistant Examiner* — David L Singer
(74) *Attorney, Agent, or Firm* — Mossman, Kumar & Tyler, PC (57) ABSTRACT

Methods, systems, and devices for determining a parameter of interest of downhole fluid using an acoustic assembly comprising a single solid acoustic transmission medium having a face immersed in the downhole fluid. Methods include using characteristics of a plurality of acoustic pulse reflections from a solid-liquid interface at the face of the solid acoustic transmission medium to estimate the parameter of interest in near real-time. The characteristics may comprise a corresponding reflection amplitude and the corresponding unique angle of reflection for each acoustic pulse reflection. Methods may include generating a two dimensional data set from measured characteristics, generating a curve by performing data fitting on the two dimensional data set, and using the reciprocal slope of the curve to estimate the parameter of interest. Methods may include estimating time-dependent values for the parameter of interest substantially continuously while the acoustic assembly is on a single logging run in the borehole.

13 Claims, 5 Drawing Sheets

(58) Field of Classification Search
CPC ... G01N 2291/02818; G01N 2291/044; G01N 29/222; G01N 29/032; G01N 29/024; G01N 29/02; G01N 29/2462; G01N 29/2468; G01N 29/4418
USPC .... 73/152.58, 579, 584, 596, 597, 599, 602, 73/627, 628, 634, 649, 589, 617, 644, 73/290 V, 598, 600; 29/594; 702/54, 55, 702/56
See application file for complete search history.

(56) References Cited

U.S. PATENT DOCUMENTS

| | | | |
|---|---|---|---|
| 4,709,357 A * | 11/1987 | Maki, Jr. | G01V 1/48 181/105 |
| 7,024,917 B2 | 4/2006 | DiFoggio | |
| 7,614,302 B2 | 11/2009 | DiFoggio et al. | |
| 2002/0014514 A1* | 2/2002 | Shimizu | B23K 31/12 228/104 |
| 2005/0204808 A1* | 9/2005 | DiFoggio | G01V 1/50 73/152.58 |
| 2005/0259512 A1* | 11/2005 | Mandal | E21B 47/082 367/10 |
| 2008/0007142 A1* | 1/2008 | Toda | G10K 11/28 310/335 |
| 2009/0138202 A1 | 5/2009 | Tang et al. | |
| 2009/0266165 A1* | 10/2009 | Greenwood | G01N 29/024 73/597 |
| 2011/0069581 A1 | 3/2011 | Krohn | |
| 2012/0109528 A1 | 5/2012 | Bolshakov et al. | |
| 2014/0169128 A1 | 6/2014 | Orban et al. | |

* cited by examiner

REFLECTION-ONLY SENSOR AT MULTIPLE ANGLES FOR NEAR REAL-TIME DETERMINATION OF ACOUSTIC PROPERTIES OF A FLUID DOWNHOLE

FIELD OF THE DISCLOSURE

This disclosure generally relates to borehole tools, and in particular to methods and apparatuses for estimating a parameter of interest of a downhole fluid.

BACKGROUND OF THE DISCLOSURE

Determining the acoustic properties of downhole fluids may be desirable for several types of downhole evaluation. Such properties may be used in characterizing the fluid itself, or for use in methods for evaluating the formation, the borehole, the casing, the cement, or for previous or ongoing operations in the borehole including exploration, development, or production.

As one example, it is known to conduct acoustic inspection of a casing cemented in a borehole to determine specific properties related to the casing and surrounding materials. For example, the bond between the cement and the casing may be evaluated, or the strength of the cement behind the casing or the casing thickness may be estimated using measurements of reflected acoustic waves, which may be generally referred to as casing cement bond logging. For many of these techniques, it is desirable that variations in fluids filling the borehole (e.g., drilling fluid) be compensated for, because conventional processing is highly sensitive to the properties of the drilling fluid.

Thus, various techniques are currently employed to determine parameters of the fluid affecting acoustic measurements, such as acoustic impedance and sound speed, in order to interpret the acoustic reflection data. Traditionally, time of flight of the acoustic signals traveling through the fluid has been used to determine sound speed, and additional measurements may be used to estimate at least one of acoustic impedance and density of the fluid.

SUMMARY OF THE DISCLOSURE

In aspects, the present disclosure is related to methods and apparatuses for estimating at least one parameter of interest of a downhole fluid relating to an earth formation intersected by a borehole.

Method embodiments for determining a parameter of interest of a downhole fluid in accordance with the present disclosure may include determining an acoustic parameter of interest of a downhole fluid using an acoustic assembly comprising a single solid acoustic transmission medium having a face immersed in the downhole fluid. Methods include using characteristics of a plurality of acoustic pulse reflections from a solid-liquid interface at the face of the solid acoustic transmission medium to estimate the parameter of interest in near real-time, wherein each acoustic pulse reflection of the plurality of acoustic pulse reflections has a corresponding unique angle of reflection with respect to the face.

The characteristics may comprise a corresponding reflection amplitude and the corresponding unique angle of reflection for each acoustic pulse reflection. Methods may include estimating the parameter of interest by determining corresponding values for $[(1-r21)/(1+r21)]^2$ and $[1/\sin^2 \phi]$ for the plurality of acoustic pulse reflections, wherein r21 is the corresponding reflection amplitude and $\phi$ is the corresponding unique angle of reflection. Methods may include generating a two dimensional data set by plotting $[(1-r21)/(1+r21)]^2$ with respect to $1/\sin^2 \phi$ for each acoustic pulse reflection, wherein r21 is the corresponding reflection amplitude and $\phi$ is the corresponding unique angle of reflection. Methods may include generating a curve by performing data fitting on the two dimensional data set. Methods may include using a slope of the curve to estimate the parameter of interest, including using a reciprocal of the slope to estimate the parameter of interest.

Methods may include transmitting acoustic pulses using at least one acoustic transducer to generate the plurality of acoustic pulse reflections. Methods may include estimating the parameter of interest independently of a time of flight in the downhole fluid of the acoustic pulses and any other acoustic pulses. The acoustic pulses and the plurality of acoustic pulse reflections may each be propagated within the single solid acoustic transmission medium. Methods may include using the at least one acoustic transducer to transmit the acoustic pulses through a second face of the single solid acoustic transmission medium. The second face may not be in contact with the downhole fluid. The at least one acoustic transducer may not be in contact with the downhole fluid. The parameter of interest may be at least one of: i) sound speed of the downhole fluid; and ii) acoustic impedance of the downhole fluid. Estimating the parameter of interest may include estimating time-dependent values for the parameter of interest substantially continuously while the acoustic assembly is on a single logging run in the borehole.

Device embodiments for determining a parameter of interest of a downhole fluid in accordance with the present disclosure may include a carrier configured to be conveyed into a borehole; a logging tool mounted on the carrier; and a processor. The logging tool may include an acoustic assembly comprising a single solid acoustic transmission medium, wherein the logging tool is configured such that when the borehole is filled with downhole fluid, the transmission medium has a corresponding face immersed in the downhole fluid; and at least one transducer configured to generate a plurality of acoustic pulse reflections from a solid-liquid interface at the face of the solid acoustic transmission medium. The processor may be configured to use characteristics of the plurality of acoustic pulse reflections to estimate the parameter of interest in near real-time. Each acoustic pulse reflection of the plurality of acoustic pulse reflections may have a corresponding unique angle of reflection with respect to the face. The apparatus may be further configured to carry out method embodiments as described herein. For example, the processor may be configured to carry out the methods described above.

Further embodiments may include a non-transitory computer-readable medium product having instructions thereon that, when executed, cause at least one processor to perform a method as described above. The non-transitory computer-readable medium product may include at least one of: (i) a ROM, (ii) an EPROM, (iii) an EEPROM, (iv) a flash memory, or (v) an optical disk.

Examples of some features of the disclosure may be summarized rather broadly herein in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

In aspects, this disclosure relates to estimating a parameter of interest of a downhole fluid in an earth formation intersected by a borehole. The at least one parameter of interest may include, but is not limited to, one or more of: (i) sound speed of the fluid, (ii) density of the fluid; and iii) acoustic impedance of the fluid.

Various techniques have been used to analyze downhole fluids. Such techniques may include the use of instruments for obtaining information relating to a parameter of interest in conjunction with sample chambers storing the sampled fluid for analysis or sample chambers allowing the fluid to pass through (continuously, or as directed by a flow control) for sampling, or as mounted on an exterior of a tool body of a downhole tool. Example systems may use a signal generator and sensor (which may be combined; e.g., a transducer) for determining acoustic impedance. In the well-known time of flight method, the sound speed, c, of a fluid may be determined by dividing the travel time of the signal through the fluid by the distance the signal traveled through the fluid.

It would be desirable to reduce the size of the measurement apparatus on a downhole tool, particularly Measurement-While-Drilling ('MWD') and Logging-While-Tripping ('LWT') tools. Design considerations for instruments used in MWD and LWT tools are particularly demanding in terms of dimensional specifications compared to wireline tools because, for MWD and LWT tools, the sensor must fit within a wall of a hollow drill collar. Various tradeoffs may be accepted in terms of design. As one example, a smaller sensor may be obtained by using a higher frequency transducer, but drilling fluids tend to be full of particles that cause dramatically increased acoustic signal attenuation in the fluid as the square of the frequency. For particle-laden drilling fluid, according to particular configurations, an upper limit for frequency may be 250 kHz or 500 kHz for transmission with acceptable attenuation through approximately 25 mm of drilling mud. Furthermore, any drilling-fluid-filled recess in a drill collar that is meant as a fluid chamber for measuring the time of flight of an acoustic pulse is at risk of "pack off," a condition in which that recess gets packed solid with cuttings and mud particulates instead of containing representative drilling fluid. Thus, configuring a traditional time-of-flight instrument for use in an MWD or LWT tool or in other space-restrictive downhole applications can be problematic depending upon the drilling fluid. Therefore, it would be desirable to create a reflection-only sensor, which does not measure any acoustic pulse that has traveled through the mud and therefore allows the use of a higher acoustic frequency (a smaller transducer) as well as avoiding the risk of fluid chamber pack off.

More recently, two acoustic transmission media each having a different acoustic impedance and/or sound speed, may be used to determine parameters of the fluid. Fluid impedance is determined from the ratio of the perpendicular reflection intensities of each media at a single glancing (non-perpendicular) reflection angle. Although this technique has advantages, the equation for determining sound speed may display sensitivities to experimental error in the measurement of the acoustic reflection amplitudes for at least one acoustic parameter (sound speed).

In the present application, only a single buffer rod (a single medium) may be used, but the reflection intensity is measured at multiple glancing angles (or at a glancing angle and a perpendicular angle). At least one acoustic transducer may be positioned to deliver acoustic pulses to the face of the media exposed to the fluid and cause reflections having multiple different reflection angles. Aspects disclosed herein enable determination of fluid sound speed using techniques that are significantly less sensitive to experimental error in the measurement of the acoustic reflection amplitudes. Aspects of the present disclosure include a reflection-only instrument for estimating parameters such as sound speed, density, and acoustic impedance of a downhole fluid (e.g., drilling fluid); time-of-flight analysis may thus be avoided with this instrument.

Embodiments may relate to the determination of a parameter of interest of a downhole fluid using an acoustic assembly with an acoustic transmission media having a face immersed in the downhole fluid. Methods may include using characteristics of a plurality of acoustic pulse reflections from a solid-liquid interface at the face of the solid acoustic transmission media to estimate the parameter of interest, wherein each acoustic pulse reflection of the plurality of acoustic pulse reflections has a corresponding unique angle of reflection with respect to the face.

Figure 1:
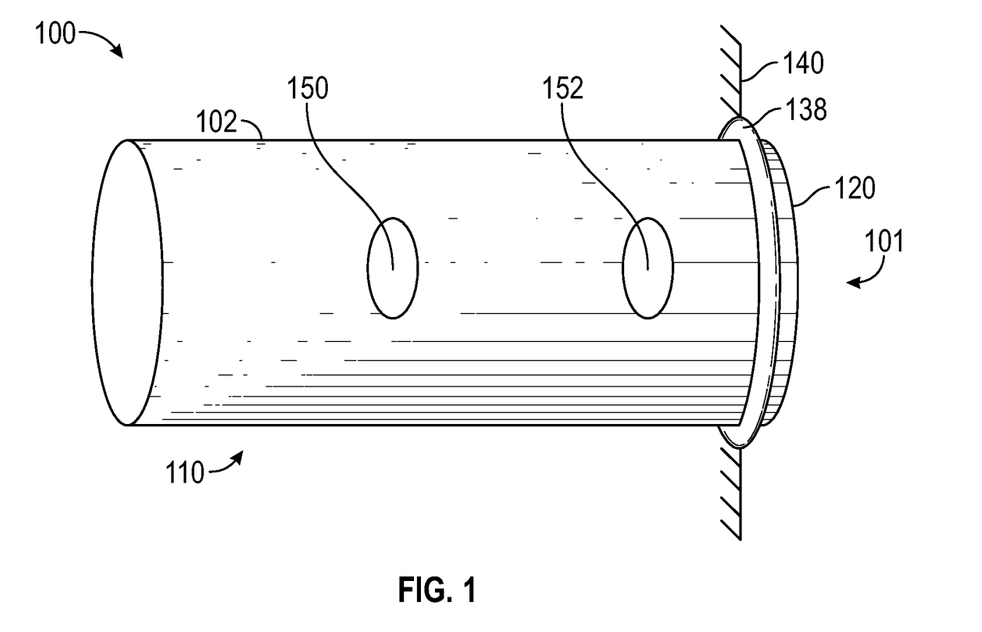
FIG. 1 shows a device in accordance with embodiments of the present disclosure.
Figure 2:
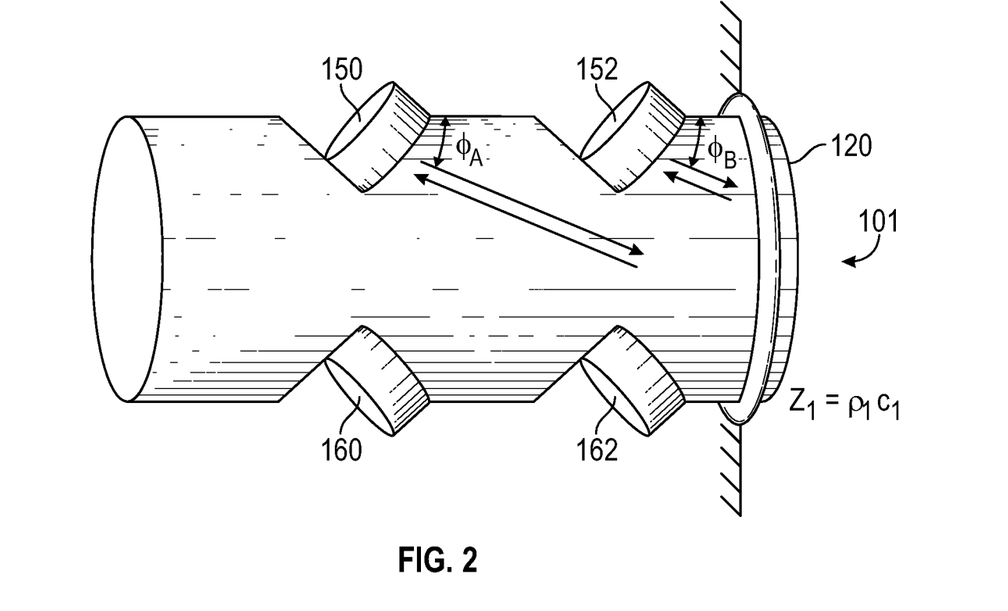
FIG. 2 shows a second view of a device in accordance with embodiments of the present disclosure.

FIGS. 1 and 2 show a device in accordance with embodiments of the present disclosure. The device 100 comprises an acoustic assembly 110 which includes a single solid acoustic transmission media 102. By solid, it is meant a media that when unconstrained holds its shape for at least the near term. At a first end of the media 102 (proximate the fluid) is a corresponding face 120 of the media 102. The device 100 is configured so that the face is immersed in the borehole fluid 101 for operation. The acoustic assembly 110 may be a substantially right circular cylinder, although other implementations may include ellipsoid or other shapes.

A plurality of acoustic transducers 150, 152 are positioned along the media, and configured to provide a plurality of acoustic pulses (not shown) that propagate within the media 102 to generate a plurality of acoustic pulse reflections. The acoustic transducers are positioned to generate pulse reflections at different angles of incidence, so that each acoustic pulse reflection of the plurality of acoustic pulse reflections has a corresponding unique angle of reflection $\phi_A$, $\phi_B$ with respect to the face 120. Although two transducers 150, 152 are shown, more transducers may be used.

Transducers 150, 152 are each configured to provide a unique non-normal incidence acoustic pulse to the face 120. Reflectors 160 and 162 are configured to return the signal to transducers 150, 152 for measurement, although two receiving transducers could also be used. Transducers 150, 152 generate information responsive to the returning acoustic reflection. Acoustic sensors may be implemented for execution in pitch-catch or pulse-echo mode. In some implementations, a single transducer's beam could be split into different parts that enter the buffer rod at different angles.

For an acoustic pulse that is traveling in a fluid of acoustic impedance $Z_2$ and then strikes a planar interface with another fluid whose acoustic impedance is $Z_1$, the reflected amplitude, $r_{21} = (A-B)/(A+B)$ where $A=(Z_2/Z_1) \sin \phi$ and $B = \text{Sqrt } [1-(c_2/c_1)^2 \cos^2 \phi]$ and the angle, $\phi$, is measured relative to the plane of the interface. This equation can be rearranged as $(B/A)^2 = [(1-r_{21})/(1+r_{21})]^2$. To put this equation into the form of $y=m\ x+b$, we can use the transform, $x=1/\sin^2 \phi$ and $y=[(1-r_{21})/(1+r_{21})]^2$ and then perform a least squares straight line fit of the collected data of y versus x. The slope of a straight line fit to the data is $m=[(c_2/c_1)^2-1](\rho_2/\rho_1)^2$ and the intercept is $b=(\rho_2/\rho_1)^2$, which together provide two equations in two unknowns that can be solved for the best fit fluid density $\rho_1 = \rho_2/\text{Sqrt }(b)$ and fluid sound speed, $c_1 = c_2/\text{Sqrt }(1+m/b)$. In the present example, the sound speed ($c_2$) and an acoustic impedance ($Z_2$) of the solid medium 102 are each different than a sound speed ($c_1$) and an acoustic impedance ($Z_1$) of the fluid 101.

However, the design of the current invention uses an acoustic pulse traveling in a solid and then being reflected at a fluid interface so, as would be expected, entering our lab data into the above liquid-liquid equations generated erroneous results. The exact equation for solid-to-liquid acoustic reflection amplitude is known (J. Krautkramer and H. Krautkramer, Ultrasonic Testing of Materials, SpringerVerlag, Third Edition, 1983, p. 606-607, Equation A.10) but that equation is very complex and cumbersome to use. The reflected longitudinal wave equation is $$R_{11} = \frac{2}{N} \left\{ \left(\frac{c_t}{c_1}\right)^2 \sin 2\alpha_1 \sin 2\alpha_t - \cos^2 2\alpha_t + \frac{\rho c}{\rho_f \rho_1} \frac{\cos \alpha_1}{\cos \alpha} \right\},$$

and for the reflected transverse wave $$R_{t1} = \frac{2}{N} \left(\frac{c_t}{c_1}\right)^2 \sin 2\alpha_1 \cos 2\alpha_t$$

where
$\alpha$=Angle of longitudinal wave in liquid
$\alpha_1$=Angle of longitudinal wave in solid
$\alpha_t$=Angle of transverse wave in solid
c=Sound speed in liquid
$c_1$=Longitudinal sound speed in solid
$c_t$=Transverse sound speed in solid
$\rho$=Density of liquid
$\rho_f$=Density of solid
This simplifies to $N=(c_t/c_1)^2 \sin 2\alpha_1 \sin 2\alpha_t + \cos^2 2\alpha_t + (\rho\ c \cos \alpha_1)/(\rho_f c_1 \cos)$.

Solving for $R_{11}$, $R_{11}=(1/N)[(c_t/c_1)^2 2(c_t/c_1) \cos \alpha'_1[1-(c_t/c_1)^2 \cos^2 \alpha'_1]^{1/2} - ([1-(c_t/c_1)^2 \cos^2 \alpha'_1]-(c_t/c_1)^2 \cos^2 \alpha'_1)^2 + (\rho\ c \sin \alpha'_1)/(\rho_f c_1 \sin \alpha')]$.

In particular embodiments, knowledge of the acoustic properties (e.g., sound speed, density, acoustic impedance) of a downhole fluid are desired for a particular time or logging depth. The acoustic properties may be used for determining or correcting other measurements at substantially the same time or depth. For these or other reasons known in the art, it may be desirable to continually update estimates of the acoustic properties of the fluid during a single logging run, such that updated estimates are available in near real-time. Derivation of such near real-time estimates is problematic under the size and processing constraints of a downhole tool using the techniques disclosed by Krautkramer.

We discovered, however, that the transforms that were useful for analyzing data from liquid-liquid reflections were also useful in correlating the solid-liquid data to liquid properties even though the liquid-liquid equations themselves were not determinative.

After generating the acoustic pulses, the reflection amplitude ($r_{21}$), for each pulse is obtained from information acquired from the transducers. The angle of reflection that the acoustic beam makes relative to the face of the buffer rod ($\phi$) is known from fabrication and calibration. For each of several known fluids, we find the best fit straight line slope, m, for a plot of $[(1-r_{21})/(1+r_{21})]^2$ versus $[1/\sin^2 \phi]$ at a plurality of angles, wherein $r_{21}$ is the corresponding reflection amplitude fraction and $\phi$ is the corresponding unique angle of reflection. We found that the various fluid sound speeds are linearly correlated with very high correlation coefficients to the reciprocals of these corresponding slopes, m. Although two reflections are shown, any number of acoustic pulses may be used as long as a plurality of angles is available.

As described above, conventional modeling of such a system, which includes mode conversion effects introduced by the solid-liquid interface, is prohibitively complex for an algorithm that we wish to use for near real-time waveform data reduction downhole using a downhole processor. For a solid-liquid interface, a portion of the compressional wave gets converted to a shear wave. A simple accounting for this interaction is problematic.

However, it has been discovered from testing various fluids that a fluid's reciprocal slope of the mathematical transform, $[(1-r_{21})/(1+r_{21})]^2$ versus $[1/\sin^2 \phi]$ may be directly correlated to sound speed and density, as shown below. The acoustic impedance, Z, of a material is its density times its sound speed.

Methods of the present disclosure may include generating a two dimensional data set by plotting $[(1-r_{21})/(1+r_{21})]^2$ with respect to $1/\sin^2 \phi$ for each acoustic pulse reflection of a plurality, wherein $r_{21}$ is the corresponding reflection amplitude and $\phi$ is the corresponding unique angle of reflection. Embodiments may include generating a curve (e.g., by data fitting) on the two dimensional data set. For example, implementations may include performing a least squares straight line fit of the curve. In operation, it is possible to estimate the fluid density and fluid sound speed from the slope of this curve. Embodiments may include calculating acoustic properties of the fluid (e.g., the sound speed of the fluid) using the reciprocal slope of $[(1-r_{21})/(1+r_{21})]^2$ with respect to $1/\sin^2 \phi$. Any number of data points may be used.

Figure 3A:
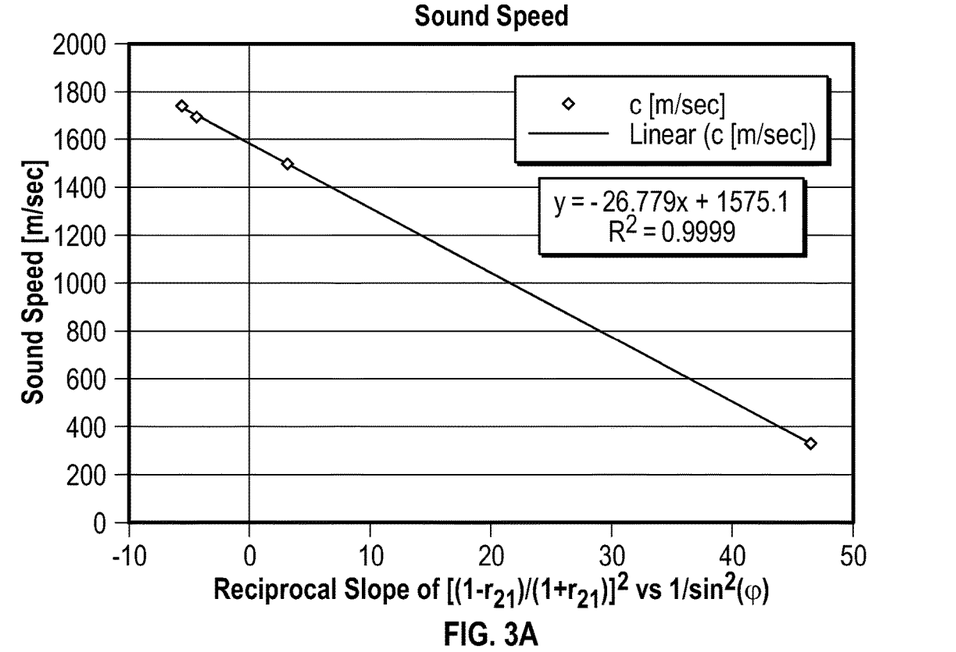
FIGS. 3A-3C illustrate correlations between reflection amplitude and fluid properties in accordance with embodiments of the present disclosure.
Figure 3B:
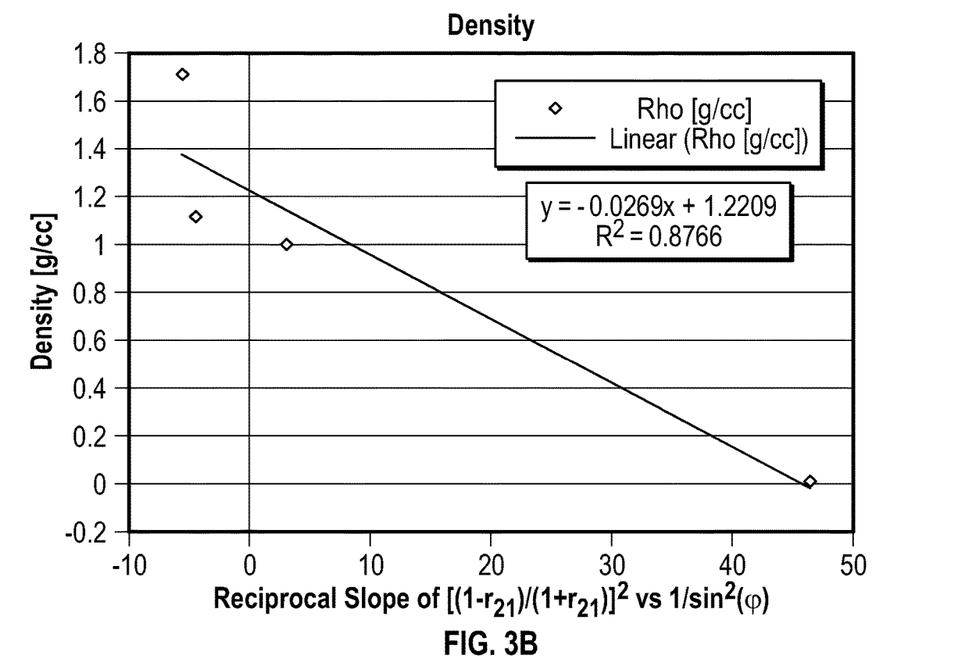
Figure 3C:
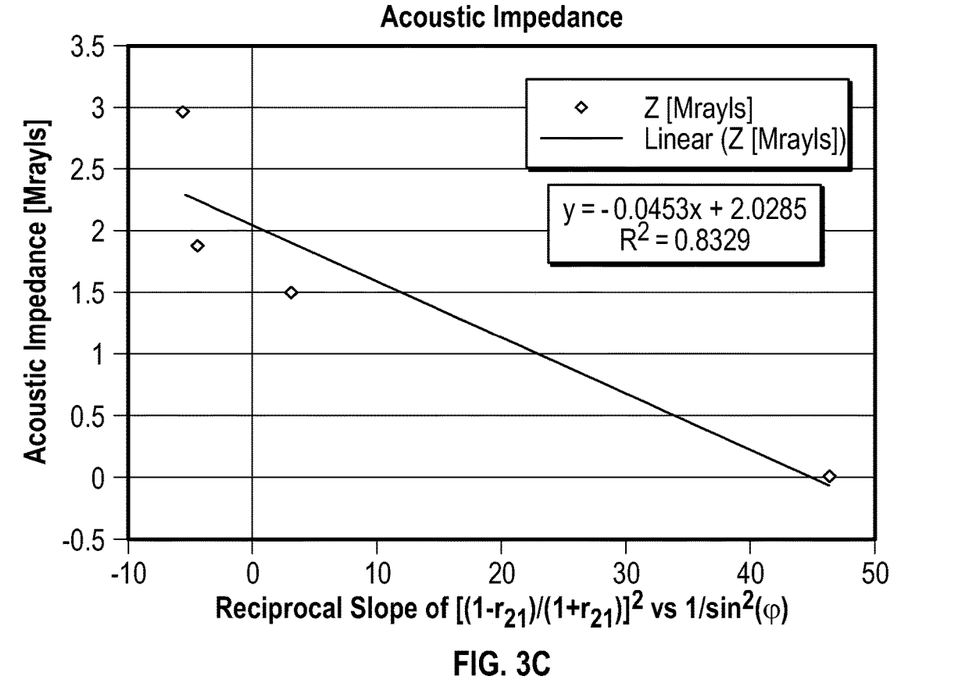

FIGS. 3A-3C illustrate correlations between reflection amplitude and fluid properties in accordance with embodiments of the present disclosure. FIG. 3A illustrates correlations between reflection amplitude and fluid sound speed. FIG. 3B illustrates correlations between reflection amplitude and density of the fluid. FIG. 3C illustrates correlations between reflection amplitude and acoustic impedance of the fluid. Table 1 compares predicted and actual fluid sound speed. Looking at the predicted and actual fluid sound speed values in Table 1 below, tests performed on four test fluids verified the relationship between reflection amplitude at various angles of incidence and sound speed. Table 2 gives the predicted and actual fluid densities, which except for air, are within about 20 percent. Table 3 gives the predicted and actual acoustic impedances, which except for air, are within about 0.5 percent.

TABLE 1

(Values in c [m/sec])

|  | air | water | antifreeze | Cs-K Fo |
|---|---|---|---|---|
| Actual | 332.00 | 1490.00 | 1685.00 | 1733.00 |
| Predicted | 331.75 | 1490.35 | 1693.20 | 1724.69 |
| Difference | −0.25 | 0.35 | 8.20 | −8.31 |
| % Error | −0.07% | 0.02% | 0.49% | −0.48% |

TABLE 2

(Values in ρ [g/cc])

|  | air | water | antifreeze | Cs-K Fo |
|---|---|---|---|---|
| Actual | 0.00124 | 1 | 1.11 | 1.708 |
| Predicted | −0.0268 | 1.136 | 1.339 | 1.371 |
| Difference | −0.0280 | 0.136 | 0.229 | −0.337 |
| % Error | −2260.30% | 13.58% | 20.66% | −19.74% |

TABLE 3

(Values in Z [MRayls])

|  | air | water | antifreeze | Cs-K Fo |
|---|---|---|---|---|
| Actual | 0.0004 | 1.49 | 1.87 | 2.96 |
| Predicted | −0.074 | 1.885 | 2.228 | 2.281 |
| Difference | −0.0746 | 0.395 | 0.358 | −0.679 |
| % Error | −18640.79% | 0.02% | 0.49% | −0.48% |

Various embodiments may use three or more transducers to generate three for more acoustic pulse reflections for use in estimating a parameter of interest in accordance with the present disclosure. Although incorporation of additional transmitters may increase cost and difficulty of maintenance, measuring reflection amplitudes at a series of reflection angles may increase accuracy of the estimated parameter. As one example, using only three angles of 40, 50, and 80 degrees, which are almost evenly spaced on a $1/\sin^2 \phi$ plot, a 10 percent uncertainty in reflection amplitude propagates as less than 1 percent uncertainty in density and sound speed.

Further, fluid sound speed can be determined from the two glancing reflection intensities without ever making any measurements upon any sound waves that might be transmitted into the fluid. That is, there may be no acoustic pulse transmitted through the fluid, or the transmitted pulse may be ignored (e.g., not measured, not used in calculation, etc.). Therefore, very small, high-frequency transducers may be used without any concern about the acoustic attenuation of the drilling fluid.

Figure 4:
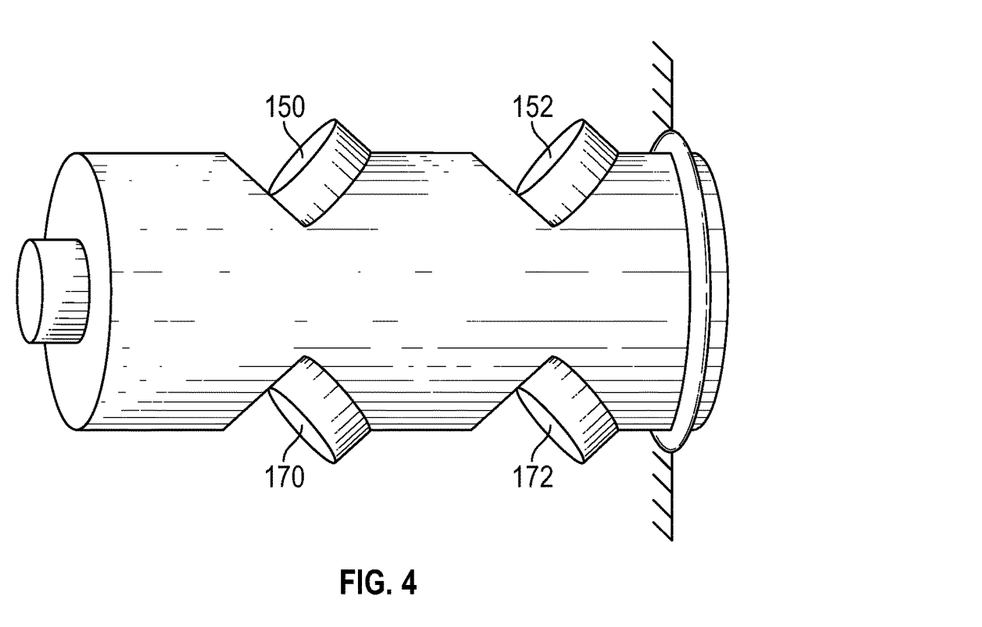
FIG. 4 illustrates another device in accordance with embodiments of the present disclosure.

FIG. 4 illustrates another device in accordance with embodiments of the present disclosure. Device 101 includes receivers 170, 172 in the place of reflectors. Receivers 170, 172 are configured to receive and measure the reflection of the non-normal pulse from the solid-liquid interface. Receivers 170, 172 may be implemented as transducers. Transducers 150, 152, 170 and 172 may be any appropriate transducer, such as, for example, piezoelectric transducers, magnetostrictive transducers, and so on, as will occur to one of skill in the art. The principal of operation is the same as that of device 100. Reflection amplitude is measured and used along with the known angle of reflection for each acoustic pulse reflection to estimate parameters of interest.

Returning to FIG. 1, device 100 is configured such that the corresponding face 120 of the acoustic assembly 110 is immersed in the downhole fluid, but the bulk of the device is not in contact with fluid. The corresponding opposite end of media 102 across from the corresponding face 120 is not in contact with the fluid; nor are transducers 150, 152. For example, seal 138 between device 100 and the tool body 140 of a logging tool (as described herein with respect to FIGS. 5 and 6) may isolate the bulk of the device from downhole fluid 101.

As shown, device 100 may be positioned substantially flush with the tool body 140. Thus, in some embodiments, corresponding face 120 may be on an outer surface of the tool, such as a drill string, such that a sample chamber or other cavity is not required. Thus, properties of the downhole fluid may be determined in-situ in the borehole, so that the fluid is unchanged by sampling or transportation processes. The substantially flush configuration also reduces the likelihood of pack off (clogging by drilling mud solids) because the face is substantially the only part of the instrument in contact with the drilling fluid. In other embodiments, the device may be configured for use in a sample chamber. The reflection-only aspects of the present disclosure enable use in size restrictive applications and allow use of higher acoustic frequencies.

In some implementations, the disclosed embodiments may be used as part of a drilling system. An example drilling system for use in conjunction with MWD and LWT is illustrated herein.

Figure 5:
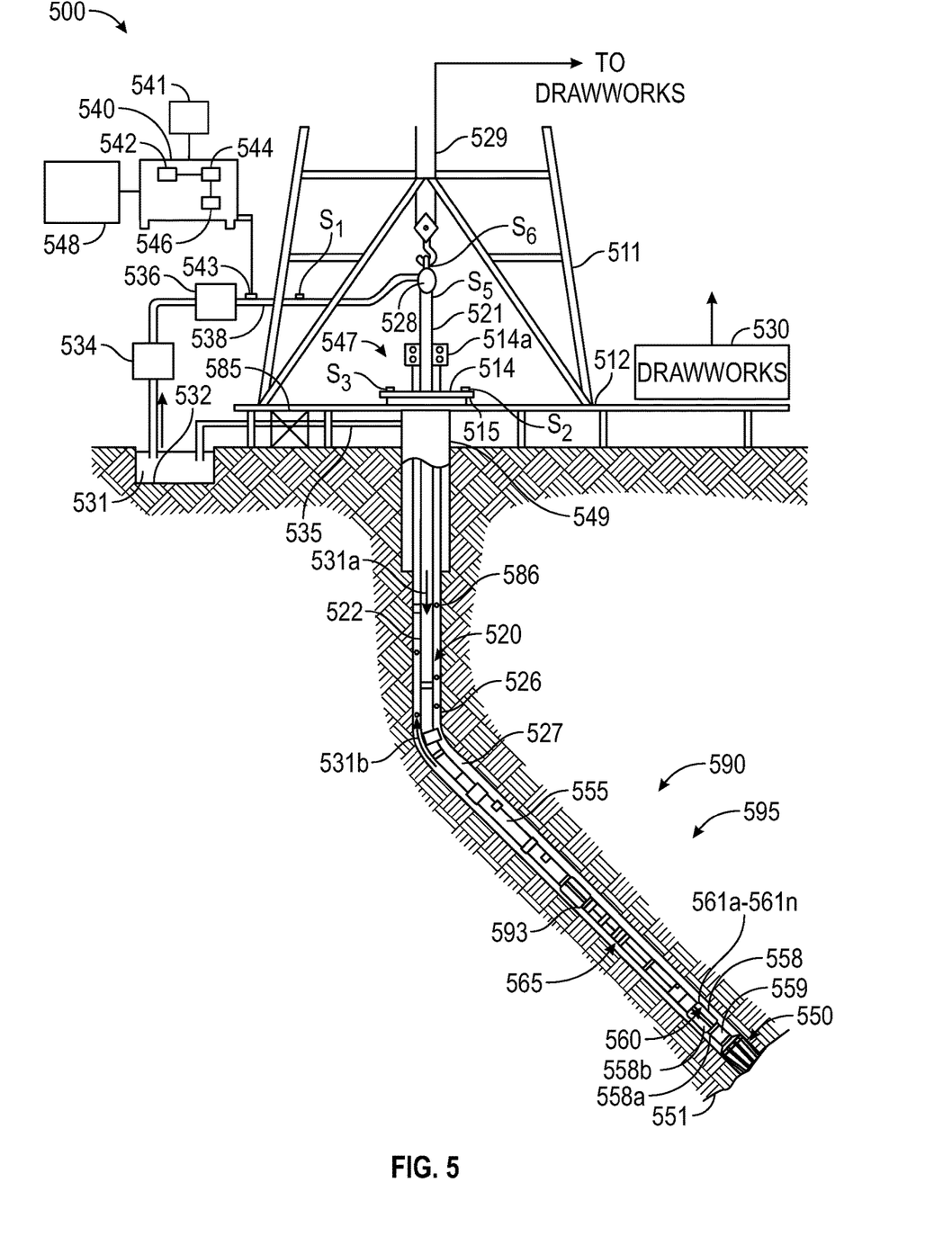
FIG. 5 is a schematic diagram of an exemplary drilling system in accordance with embodiments of the present disclosure.

FIG. 5 is a schematic diagram of an exemplary drilling system 500 according to one embodiment of the disclosure. FIG. 5 schematically illustrates a drilling system 500 configured to acquire information for downhole fluid analysis in a borehole intersecting a formation using a test apparatus; drilling system 500 includes a drill string 520 that includes a bottomhole assembly (BHA) 590 conveyed in a borehole 526. The drilling system 500 includes a conventional derrick 511 erected on a platform or floor 512 which supports a rotary table 514 that is rotated by a prime mover, such as an electric motor (not shown), at a desired rotational speed. A tubing (such as jointed drill pipe 522), having the drilling assembly 590, attached at its bottom end extends from the surface to the bottom 551 of the borehole 526. A drill bit 550, attached to drilling assembly 590, disintegrates the geological formations when it is rotated to drill the borehole 526. The drill string 520 is coupled to a drawworks 530 via a Kelly joint 521, swivel 528 and line 529 through a pulley. Drawworks 530 is operated to control the weight on bit ("WOB"). The drill string 520 may be rotated by a top drive (not shown) instead of by the prime mover and the rotary table 514. Alternatively, a coiled-tubing may be used as the tubing 522. A tubing injector 514a may be used to convey the coiled-tubing having the drilling assembly attached to its bottom end. The operations of the drawworks 530 and the tubing injector 514a are known in the art and are thus not described in detail herein.

A suitable drilling fluid 531 (also referred to as the "mud") from a source 532 thereof, such as a mud pit, may be circulated under pressure through the drill string 520 by a mud pump 534. The drilling fluid 531 passes from the mud pump 534 into the drill string 520 via a desurger 536 and the fluid line 538. The drilling fluid 531a from the drilling tubular discharges at the borehole bottom 551 through openings in the drill bit 550. The returning drilling fluid 531b circulates uphole through the annular space 527 between the drill string 520 and the borehole 526 and returns to the mud pit 532 via a return line 535 and drill cutting screen 585 that removes the drill cuttings 586 from the returning drilling fluid 531b. A sensor S1 in line 538 provides information about the fluid flow rate. A surface torque sensor S2 and a sensor S3 associated with the drill string 520 respectively provide information about the torque and the rotational speed of the drill string 520. Tubing injection speed is determined from the sensor S5, while the sensor S6 provides the hook load of the drill string 520.

Well control system 547 is placed at the top end of the borehole 526. The well control system 547 includes a surface blow-out-preventer (BOP) stack 515 and a surface choke 549 in communication with a wellbore annulus 527. The surface choke 549 can control the flow of fluid out of the borehole 526 to provide a back pressure as needed to control the well.

In some applications, the drill bit 550 is rotated by only rotating the drill pipe 522. However, in many other applications, a downhole motor 555 (mud motor) disposed in the BHA 590 also rotates the drill bit 550. The rate of penetration (ROP) for a given BHA largely depends on the WOB or the thrust force on the drill bit 550 and its rotational speed.

A surface control unit or controller 540 receives signals from the downhole sensors and devices via a sensor 543 placed in the fluid line 538 and signals from sensors S1-S6 and other sensors used in the system 500 and processes such signals according to programmed instructions provided to the surface control unit 540. The surface control unit 540 displays desired drilling parameters and other information on a display/monitor 541 that is utilized by an operator to control the drilling operations. The surface control unit 540 may be a computer-based unit that may include a processor 542 (such as a microprocessor), a storage device 544, such as a solid-state memory, tape or hard disc, and one or more computer programs 546 in the storage device 544 that are accessible to the processor 542 for executing instructions contained in such programs. The surface control unit 540 may further communicate with a remote control unit 548. The surface control unit 540 may process data relating to the drilling operations, data from the sensors and devices on the surface, data received from downhole, and may control one or more operations of the downhole and surface devices. The data may be transmitted in analog or digital form.

The BHA 590 may also contain formation evaluation sensors or devices (also referred to as measurement-while-drilling ("MWD") or logging-while-drilling ("LWD") sensors) determining resistivity, density, porosity, permeability, acoustic properties, nuclear-magnetic resonance properties, formation pressures, properties or characteristics of the fluids downhole and other desired properties of the formation 595 surrounding the BHA 590. Such sensors are generally known in the art and for convenience are generally denoted herein by numeral 565. The BHA 590 may further include a variety of other sensors and devices 559 for determining one or more properties of the BHA 590 (such as vibration, bending moment, acceleration, oscillations, whirl, stick-slip, etc.), drilling operating parameters (such as weight-on-bit, fluid flow rate, pressure, temperature, rate of penetration, azimuth, tool face, drill bit rotation, etc.).

The BHA 590 may include a steering apparatus or tool 558 for steering the drill bit 550 along a desired drilling path. In one aspect, the steering apparatus may include a steering unit 560, having a number of force application members 561a-561n. The force application members may be mounted directly on the drill string, or they may be at least partially integrated into the drilling motor. In another aspect, the force application members may be mounted on a sleeve, which is rotatable about the center axis of the drill string. The force application members may be activated using electro-mechanical, electro-hydraulic or mud-hydraulic actuators. In yet another embodiment the steering apparatus may include a steering unit 558 having a bent sub and a first steering device 558a to orient the bent sub in the wellbore and the second steering device 558b to maintain the bent sub along a selected drilling direction. The steering unit 558, 560 may include near-bit inclinometers and magnetometers.

The drilling system 500 may include sensors, circuitry and processing software and algorithms for providing information about desired drilling parameters relating to the BHA, drill string, the drill bit and downhole equipment such as a drilling motor, steering unit, thrusters, etc. Many current drilling systems, especially for drilling highly deviated and horizontal wellbores, utilize coiled-tubing for conveying the drilling assembly downhole. In such applications a thruster may be deployed in the drill string 520 to provide the required force on the drill bit.

Exemplary sensors for determining drilling parameters include, but are not limited to drill bit sensors, an RPM sensor, a weight on bit sensor, sensors for measuring mud motor parameters (e.g., mud motor stator temperature, differential pressure across a mud motor, and fluid flow rate through a mud motor), and sensors for measuring acceleration, vibration, whirl, radial displacement, stick-slip, torque, shock, vibration, strain, stress, bending moment, bit bounce, axial thrust, friction, backward rotation, BHA buckling, and radial thrust. Sensors distributed along the drill string can measure physical quantities such as drill string acceleration and strain, internal pressures in the drill string bore, external pressure in the annulus, vibration, temperature, electrical and magnetic field intensities inside the drill string, bore of the drill string, etc. Suitable systems for making dynamic downhole measurements include COPILOT, a downhole measurement system, manufactured by BAKER HUGHES INCORPORATED.

The drilling system 500 can include one or more downhole processors at a suitable location such as 593 on the BHA 590. The processor(s) can be a microprocessor that uses a computer program implemented on a suitable non-transitory computer-readable medium that enables the processor to perform the control and processing. The non-transitory computer-readable medium may include one or more ROMs, EPROMs, EAROMs, EEPROMs, Flash Memories, RAMs, Hard Drives and/or Optical disks. Other equipment such as power and data buses, power supplies, and the like will be apparent to one skilled in the art. In one embodiment, the MWD system utilizes mud pulse telemetry to communicate data from a downhole location to the surface while drilling operations take place.

While a drill string 520 is shown as a carrier (conveyance device) for sensors 565, it should be understood that embodiments of the present disclosure may be used in connection with tools conveyed via rigid (e.g. jointed tubular or coiled tubing) as well as non-rigid (e. g. wireline, slickline, e-line, etc.) conveyance systems. The drilling system 500 may include a bottomhole assembly and/or sensors and equipment for implementation of embodiments of the present disclosure on either a drill string or a wireline.

A point of novelty of the system illustrated in FIG. 5 is that the surface processor 542 and/or the downhole processor 593 are configured to perform certain methods (discussed below) that are not in the prior art. Surface processor 542 or downhole processor 593 may be configured to control components of the drilling system 500. Surface processor 542 or downhole processor 593 may be configured to control sensors described above and to estimate a parameter of interest according to methods described herein. Control of these devices, and of the various processes of the drilling system generally, may be carried out in a completely automated fashion or through interaction with personnel via notifications, graphical representations, user interfaces and the like. Reference information accessible to the processor may also be used.

More specifically, drill string 520 (or BHA 590) may include an apparatus for estimating one or more parameters of the downhole fluid. For convenience, such apparatus may be denoted by numeral 559 or 565, and may comprise device 100 or other devices or tools in accordance with embodiments of the present disclosure. In some general embodiments, surface processor 542, downhole processor 593, or other processors (e.g. remote processors) may be configured to use the apparatus to produce information indicative of the downhole fluid, such as, for example, drilling fluid. One of the processors may also be configured to estimate from the information a parameter of interest of the downhole fluid.

In some embodiments, drill string 520 may include an acoustic logging apparatus configured for evaluating the cement bond occupying the annular space between the casing and the borehole wall, as described in greater detail below with reference to FIG. 6. For convenience, such apparatus may be denoted by numeral 559 or 565. In some general embodiments, surface processor 542, downhole processor 593, or other processors (e.g. remote processors) may be configured to use the acoustic logging apparatus to produce information indicative of the properties of the cement bond.

In some embodiments, processors may include electromechanical and/or electrical circuitry configured to control one or more components of the tool apparatus. In other embodiments, processors may use algorithms and programming to receive information and control operation of the apparatus. Therefore, processors may include an information processor that is in data communication with a data storage medium and a processor memory. The data storage medium may be any standard computer data storage device, such as a USB drive, memory stick, hard disk, removable RAM, EPROMs, EAROMs, flash memories and optical disks or other commonly used memory storage system known to one of ordinary skill in the art including Internet based storage. The data storage medium may store one or more programs that when executed causes information processor to execute the disclosed method(s). Herein, "information" may include raw data, processed data, analog signals, and digital signals.

As described above, carriers such as coiled tubing, slickline, e-line, wireline, and so one may be used in connection with the techniques disclosed herein. In some embodiments, the sensor described herein may be implemented as a sampling and measuring instrument, such as, for example, one employing a probe. Specific configuration of the components with respect to one another may vary.

Figure 6:
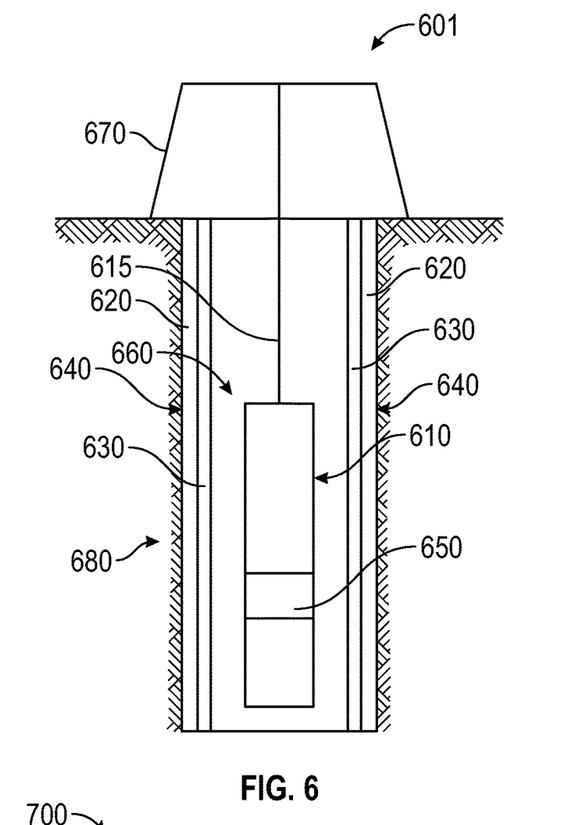
FIG. 6 illustrates an acoustic logging tool in accordance with embodiments of the present disclosure.

FIG. 6 illustrates an acoustic logging tool in accordance with embodiments of the present disclosure. The tool 610 is configured to be conveyed in a borehole intersecting a formation 680. The borehole wall 640 is lined with casing 630 filled with a downhole fluid 660, such as, for example, drilling fluid. Cement 620 fills the annulus between the borehole wall 640 and the casing 630. In one illustrative embodiment, the tool 610 may contain a sensor unit 650, including, for example, one or more acoustic transmitters and receivers (e.g., transducers), configured for evaluation of the cement bond existing between the system of the casing 630, the borehole wall 640, and the cement 620 according to known techniques. For example, electronics in the tool 610, at the surface, and/or elsewhere in system 601 (e.g., at least one processor) may be configured to use acoustic measurements to determine properties of the cement bond using known techniques, such as, for example, analysis of casing resonance.

The system 601 may include a conventional derrick 670. A conveyance device (carrier 615) which may be rigid or non-rigid, may be configured to convey the downhole tool 610 into wellbore 640 in proximity to formation 680. The carrier 615 may be a drill string, coiled tubing, a slickline, an e-line, a wireline, etc. Downhole tool 610 may be coupled or combined with additional tools (e.g., some or all the information processing system of FIG. 5). Thus, depending on the configuration, the tool 610 may be used during drilling and/or after the wellbore (borehole) 640 has been formed. While a land system is shown, the teachings of the present disclosure may also be utilized in offshore or subsea applications. The carrier 615 may include embedded conductors for power and/or data for providing signal and/or power communication between the surface and downhole equipment. The carrier 615 may include a bottom hole assembly, which may include a drilling motor for rotating a drill bit.

Figure 7:
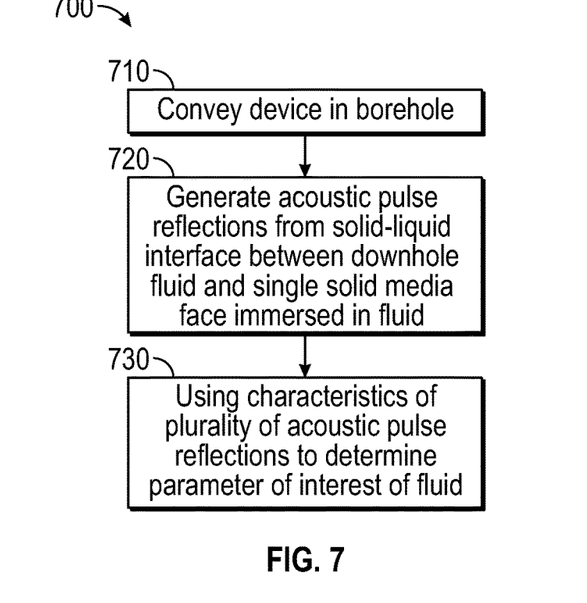
FIG. 7 shows a flow chart of a method for estimating a parameter of interest in an earth formation intersected by a borehole in accordance with embodiments of the present disclosure.

FIG. 7 shows a flow chart of a method 700 for estimating a parameter of interest in an earth formation intersected by a borehole according to one embodiment of the present disclosure. The method 700 may include using device 100 or the like. In step 710, an acoustic assembly 110 which includes a single solid acoustic transmission media 102 is conveyed into the borehole. For example, the acoustic assembly may be conveyed using conveyance device (or carrier) 615. The optical displacement device may be incorporated as an instrument in a downhole logging tool.

In step 720, the device may be used to generate information relating to characteristics of a downhole fluid. For example, a plurality of acoustic pulse reflections may be generated by transmitting acoustic pulses into a single solid acoustic transmission media having a face immersed in the downhole fluid, wherein each acoustic pulse reflection of the plurality of acoustic pulse reflections has a corresponding unique angle of reflection with respect to the face. Characteristics of the pulse reflections may be estimated using transducer response to the pulses.

In step 730, the method includes using characteristics of a plurality of acoustic pulse reflections to determine a parameter of interest of the downhole fluid. As described above, this may be carried out by estimating the parameter of interest as a function of $[(1-r_{21})/(1+r_{21})]^2$ and $[1/\sin^2 \phi]$ for the plurality of acoustic pulse reflections, wherein $r_{21}$ is the corresponding reflection amplitude and $\phi$ is the corresponding unique angle of reflection. For example, the method may include generating a two dimensional data set by plotting $[(1-r_{21})/(1+r_{21})]^2$ with respect to $1/\sin^2 \phi$ for each acoustic pulse reflection and generating a curve by performing data fitting on the two dimensional data set. Estimating the parameter of interest may include using a model correlating the function above with sound speed, density, acoustic impedance, and so on of the fluid. Estimating the parameter of interest may be carried out in near-real time. In one example, the model may relate a parameter of interest (e.g., sound speed) and the reciprocal slope of transform $[(1-r_{21})/(1+r_{21})]^2$ versus $[1/\sin^2 \phi]$. This step may also involve the use of reference information. In some embodiments, some or all of the steps herein may be carried out iteratively to periodically or intermittently estimate values for the parameter of interest while the acoustic assembly is on a single logging run in the borehole. The estimation may be contingent upon particular events. The period or triggering event may vary by implementation, as well known in the art. For example, estimation may take place in connection with additional measurements (e.g., CCB log measurements) for which the parameter of interest is desired. In some implementations, due to the lean nature of processing requirements time-dependent values for the parameter of interest may be estimated (e.g, via a downhole processor) substantially continuously while the acoustic assembly is on a single logging run in the borehole.

For convenience, certain definitions are now presented. The term "acoustic signal" relates to the pressure amplitude versus time of a sound wave or an acoustic wave traveling in a medium that allows propagation of such waves. In one embodiment, the acoustic signal can be a pulse. The term "acoustic transducer" relates to a device for transmitting (i.e., generating) an acoustic signal or receiving an acoustic signal. When receiving the acoustic signal in one embodiment, the acoustic transducer converts the energy of the acoustic signal into electrical energy. The electrical energy has a waveform that is related to a waveform of the acoustic signal.

The term "carrier" (or "conveyance device") as used above means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other carrier examples include casing pipes, wirelines, wireline sondes, slickline sondes, drop shots, downhole subs, BHA's, drill string inserts, modules, internal housings and substrate portions thereof, self-propelled tractors. As used above, the term "sub" refers to any structure that is configured to partially enclose, completely enclose, house, or support a device. The term "information" as used above includes any form of information (analog, digital, EM, printed, etc.). The term "processor" herein includes, but is not limited to, any device that transmits, receives, manipulates, converts, calculates, modulates, transposes, carries, stores or otherwise utilizes information. A processor refers to any circuitry performing the above, and may include a microprocessor, resident memory, and/or peripherals for executing programmed instructions, application specific integrated circuits (ASICs), field programmable gate arrays (FPGAs), or any other circuitry configured to execute logic to perform methods as described herein. Fluid, as described herein, may refer to a liquid, a gas, a mixture, and so on.

The term "near real-time" as applied to methods of the present disclosure refers to an action performed while the instrument is still downhole, after the generation of the pulse reflection and prior to movement of the tool a distance of 100 meters, 50 meters, 25 meters, 10 meters, 1 meter, or less; and may be defined as estimation of the parameter of interest within 15 minutes of generating the pulse reflection, within 10 minutes of generation, within 5 minutes of generation, within 3 minutes of generation, within 2 minutes of generation, within 1 minute of generation, or less.

The term "in-situ" as applied herein to evaluating acoustical properties of downhole fluids refers to evaluation of the fluids in the borehole (and while exterior to the tool) prior to exposure to external influences, e.g., fluid in an interval of the annulus between the borehole and the tool. By "substantially continuously," it is meant at intervals of time sufficiently small so that granularity of measurement does not appreciably affect the accuracy of determination of a related property, examples of such an interval being, for example, less than 1 minute, less than 10 seconds, less than 1 second, less than 100 milliseconds, less than 10 milliseconds, less than 1 millisecond, and so on.

Non-limiting examples of downhole fluids include drilling fluids, return fluids, formation fluids, production fluids containing one or more hydrocarbons, oils and solvents used in conjunction with downhole tools, water, brine, engineered fluids, and combinations thereof. The tool may contain a formation test apparatus according to the present disclosure, which will be described in greater detail below.

While the disclosure has been described with reference to example embodiments, it will be understood that various changes may be made and equivalents may be substituted for elements thereof without departing from the scope of the disclosure. In addition, many modifications will be appreciated to adapt a particular instrument, situation or material to the teachings of the disclosure without departing from the essential scope thereof. Further embodiments may include direct measurement wireline embodiments, drilling embodiments employing a sample chamber, LWT tools, including drop subs and the like, and so on. While the present disclosure is discussed in the context of a hydrocarbon producing well, it should be understood that the present disclosure may be used in any borehole environment (e.g., a geothermal well) with any type of downhole fluid.

While the foregoing disclosure is directed to particular embodiments, various modifications will be apparent to those skilled in the art. It is intended that all variations be embraced by the foregoing disclosure.

What is claimed is:

1. A method of estimating an acoustic parameter of interest of a downhole fluid using an acoustic assembly comprising a single solid acoustic transmission medium having a face immersed in the downhole fluid, the method comprising:

using at least one acoustic transducer acoustically coupled to the single solid acoustic transmission medium to transmit and receive acoustic pulses, including generating a plurality of acoustic pulse reflections from a solid-liquid interface at the face of the single solid acoustic transmission medium, and receiving the plurality of acoustic pulse reflections;

estimating the parameter of interest in near real-time utilizing characteristics of the plurality of acoustic pulse reflections from the solid-liquid interface, wherein each acoustic pulse reflection of the plurality of acoustic pulse reflections has a corresponding unique angle of reflection with respect to the face;

wherein the characteristics comprise a corresponding reflection amplitude and the corresponding unique angle of reflection for each acoustic pulse reflection, and wherein the parameter of interest is at least one of: i) sound speed of the downhole fluid; ii) density of the downhole fluid; and iii) acoustic impedance of the downhole fluid.

2. The method of claim 1, wherein the step of estimating the parameter of interest in near real-time utilizing characteristics of the plurality of acoustic pulse reflections comprises estimating the parameter of interest by determining corresponding values for $[(1-r_{21})/(1+r_{21})]^2$ and $[1/\sin^2 \phi]$ for the plurality of acoustic pulse reflections, wherein $r_{21}$ is the corresponding reflection amplitude and $\phi$ is the corresponding unique angle of reflection.

3. The method of claim 1, comprising generating a two dimensional data set by plotting $[(1-r_{21})/(1+r_{21})]^2$ with respect to $1/\sin^2 \phi$ for each acoustic pulse reflection, wherein $r_{21}$ is the corresponding reflection amplitude and $\phi$ is the corresponding unique angle of reflection.

4. The method of claim 3, comprising generating a curve by performing data fitting on the two dimensional data set.

5. The method of claim 4, wherein the step of estimating the parameter of interest in near real-time utilizing characteristics of the plurality of acoustic pulse reflections comprises estimating the parameter of interest in near real-time utilizing a slope of the curve.

6. The method of claim 5, wherein the step of estimating the parameter of interest in near real-time utilizing characteristics of the plurality of acoustic pulse reflections comprises estimating the parameter of interest in near real-time utilizing a reciprocal of the slope.

7. The method of claim 1, wherein the step of estimating the parameter of interest in near real-time utilizing characteristics of the plurality of acoustic pulse reflections comprises estimating the parameter of interest independently of a time of flight in the downhole fluid of the acoustic pulses and any other acoustic pulses.

8. The method of claim 1, wherein the acoustic pulses and the plurality of acoustic pulse reflections are each propagated within the single solid acoustic transmission medium.

9. The method of claim 1, wherein the step of transmitting acoustic pulses comprises using the at least one acoustic transducer to transmit the acoustic pulses through a second face of the single solid acoustic transmission medium.

10. The method of claim 9, wherein the second face is not in contact with the downhole fluid.

11. The method of claim 1, wherein the at least one acoustic transducer is not in contact with the downhole fluid.

12. The method of claim 1, wherein estimating the parameter of interest comprises estimating time-dependent values for the parameter of interest substantially continuously while the acoustic assembly is on a single logging run in the borehole.

13. An apparatus for estimating a parameter of interest of a downhole fluid, the apparatus comprising:
  a carrier configured to be conveyed into a borehole;
  a logging tool mounted on the carrier, the logging tool including an acoustic assembly comprising a single solid acoustic transmission medium and at least one acoustic transducer, wherein the logging tool is configured such that when the borehole is filled with downhole fluid, the transmission medium has a corresponding face immersed in the downhole fluid, and the at least one acoustic transducer is acoustically coupled to the single solid acoustic transmission medium to transmit and receive acoustic pulses, including generating a plurality of acoustic pulse reflections from a solid-liquid interface at the face of the single solid acoustic transmission medium, and receiving the plurality of acoustic pulse reflections; and
  a processor configured to estimate the parameter of interest in near real-time utilizing characteristics of the plurality of acoustic pulse reflections from the solid-liquid interface;
  wherein each acoustic pulse reflection of the plurality of acoustic pulse reflections has a corresponding unique angle of reflection with respect to the face;
  wherein the characteristics comprise a corresponding reflection amplitude and the corresponding unique angle of reflection for each acoustic pulse reflection, and
  wherein the parameter of interest is at least one of: i) sound speed of the downhole fluid; ii) density of the downhole fluid; and iii) acoustic impedance of the downhole fluid.

* * * * *